(12) United States Patent
Takei et al.

(10) Patent No.: US 11,807,264 B2
(45) Date of Patent: Nov. 7, 2023

(54) DRIVING ASSISTANCE APPARATUS, DRIVING ASSISTANCE METHOD, AND MEDIUM

(71) Applicant: JVCKENWOOD Corporation, Yokohama (JP)

(72) Inventors: Hiroyuki Takei, Yokohama (JP); Masaru Ninomiya, Yokohama (JP); Shuji Hakoshima, Yokohama (JP); Miku Komurata, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 0 days.

(21) Appl. No.: 17/586,841

(22) Filed: Jan. 28, 2022

(65) Prior Publication Data

US 2022/0144302 A1 May 12, 2022

Related U.S. Application Data

(63) Continuation of application No. PCT/JP2020/040079, filed on Oct. 26, 2020.

(30) Foreign Application Priority Data

Oct. 31, 2019 (JP) .................. 2019-198154

(51) Int. Cl.
*B60W 50/16* (2020.01)
*G06V 20/58* (2022.01)
(Continued)

(52) U.S. Cl.
CPC ............ *B60W 50/16* (2013.01); *B60W 40/04* (2013.01); *B60W 40/08* (2013.01); *G06V 20/58* (2022.01);
(Continued)

(58) Field of Classification Search
CPC ...... B60W 50/16; B60W 40/04; B60W 40/08; B60W 2050/143; B60W 2050/146;
(Continued)

(56) References Cited

U.S. PATENT DOCUMENTS

2010/0316255 A1* 12/2010 Mathony ............ G08G 1/09675
340/439
2017/0166122 A1* 6/2017 Ando .................... G06V 20/582
(Continued)

FOREIGN PATENT DOCUMENTS

| EP | 2821978 | 1/2015 |
| JP | 2007-133692 | 5/2007 |

(Continued)

OTHER PUBLICATIONS

International Search Report and Written Opinion for International Application No. PCT/JP2020/040079 dated Dec. 28, 2020, 9 pages.

*Primary Examiner* — Mohamed Barakat
(74) *Attorney, Agent, or Firm* — AMIN, TUROCY & WATSON, LLP

(57) ABSTRACT

A driving assistance apparatus includes: a driver identifying unit that identifies a driver driving a vehicle; an evaluation data obtaining unit that obtains, based on an identification result of the driver identifying unit, evaluation data on the driver's visual cognitive ability for an event that occurs when the driver is driving the vehicle; an event detecting unit that detects, on the basis of surrounding information data indicating a situation of the vehicle's surroundings, whether or not the event has occurred; and a processing unit that determines, in a case where the event has been detected and on the basis of the evaluation data on the driver, the evaluation data being related to the event, whether or not notification information is to be output from an output unit.

7 Claims, 9 Drawing Sheets

(51) Int. Cl.
  *G06V 20/59* (2022.01)
  *B60W 40/04* (2006.01)
  *B60W 40/08* (2012.01)
  *B60W 50/14* (2020.01)

(52) U.S. Cl.
  CPC ..... *G06V 20/597* (2022.01); *B60W 2050/143* (2013.01); *B60W 2050/146* (2013.01); *B60W 2540/043* (2020.02); *B60W 2540/221* (2020.02); *B60W 2540/225* (2020.02); *B60W 2540/229* (2020.02)

(58) Field of Classification Search
  CPC ..... B60W 2540/043; B60W 2540/221; B60W 2540/225; B60W 2540/229; G06V 20/58; G06V 20/597; G06V 20/56; A61B 3/113; A61B 5/18; G08G 1/16
  See application file for complete search history.

(56) References Cited

U.S. PATENT DOCUMENTS

2020/0180612 A1* 6/2020 Finelt .................. G06V 20/58
2021/0016805 A1* 1/2021 Oba ..................... G06T 3/00

FOREIGN PATENT DOCUMENTS

| | | | | |
|---|---|---|---|---|
| JP | 2019-114100 | | 7/2019 | |
| JP | 2019114100 A | * | 7/2019 | |
| WO | 2013/128920 | | 9/2013 | |
| WO | WO-2013128920 A1 | * | 9/2013 | ............ B60W 40/09 |

* cited by examiner

DRIVING ASSISTANCE APPARATUS, DRIVING ASSISTANCE METHOD, AND MEDIUM

CROSS-REFERENCE TO RELATED APPLICATION

This application is a Continuation of PCT International Application No. PCT/JP2020/040079 filed on Oct. 26, 2020 which claims the benefit of priority from Japanese Patent Application No. 2019-198154 filed on Oct. 31, 2019, the entire contents of both of which are incorporated herein by reference.

BACKGROUND

1. Technical Field

The present disclosure relates to a driving assistance apparatus, a driving assistance method, and a medium.

2. Description of the Related Art

Driving assistance apparatuses for assisting drivers driving vehicles, such as cars, have been known. These known driving assistance apparatuses include, for example, a driving behavior evaluation apparatus for detecting driving behavior of a driver and evaluating whether or not the driver's safety check action is appropriate (see, for example, Japanese Unexamined Patent Application Publication No. 2007-133692 A).

In recent years, traffic accidents are frequently caused by elderly drivers, for example, who have deteriorated in physical function, such as visual cognitive ability. There is thus a demand for driving assistance according to a driver's visual cognitive ability in order to prevent such accidents.

SUMMARY

It is an object of the present disclosure to at least partially solve the problems in the conventional technology.

A driving assistance apparatus according to the present disclosure, includes a driver identifying unit that identifies a driver driving a vehicle, an evaluation data obtaining unit that obtains, based on an identification result of the driver identifying unit, evaluation data on the driver's visual cognitive ability for an event that occurs when the driver is driving the vehicle, an event detecting unit that detects whether or not the event has occurred, on the basis of surrounding information data indicating a situation of the vehicle's surroundings, and a processing unit that determines, in a case where the event has been detected and on the basis of the evaluation data on the driver, the evaluation data being related to the event, whether or not notification information is to be output from an output unit, and causes the output unit to output the notification information in a case where the processing unit has determined that the notification information is to be output.

A driving assistance method according to the present disclosure, includes identifying a driver driving a vehicle, obtaining, based on an identification result of the identifying, evaluation data on the driver's visual cognitive ability for an event that occurs when the driver is driving the vehicle, detecting whether or not the event has occurred, on the basis of surrounding information data indicating a situation of the vehicle's surroundings, and determining, in a case where the event has been detected and on the basis of the evaluation data on the driver, the evaluation data being related to the event, whether or not notification information is to be output from an output unit, and causing the output unit to output the notification information in a case where it has been determined that the notification information is to be output.

A non-transitory computer readable recording medium storing therein a driving assistance program according to the present disclosure is disclosed. The driving assistance program causes a computer to execute a process of identifying a driver driving a vehicle, a process of obtaining, based on an identification result of the identifying, evaluation data on the driver's visual cognitive ability for an event that occurs when the driver is driving the vehicle, a process of detecting whether or not the event has occurred, on the basis of surrounding information data indicating a situation of the vehicle's surroundings, and a process of determining, in a case where the event has been detected and on the basis of the evaluation data on the driver, the evaluation data being related to the event, whether or not notification information is to be output from an output unit, and causing the output unit to output the notification information in a case where it has been determined that the notification information is to be output.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION OF THE PREFERRED EMBODIMENTS

An embodiment of a driving assistance apparatus, a driving assistance method, and a driving assistance program according to the present disclosure will hereinafter be described on the basis of the drawings. The disclosure is not limited by this embodiment. Furthermore, components in the following embodiment include those that can be easily substituted by persons skilled in the art or those that are substantially the same.

Driving Assistance Apparatus

Figure 1:
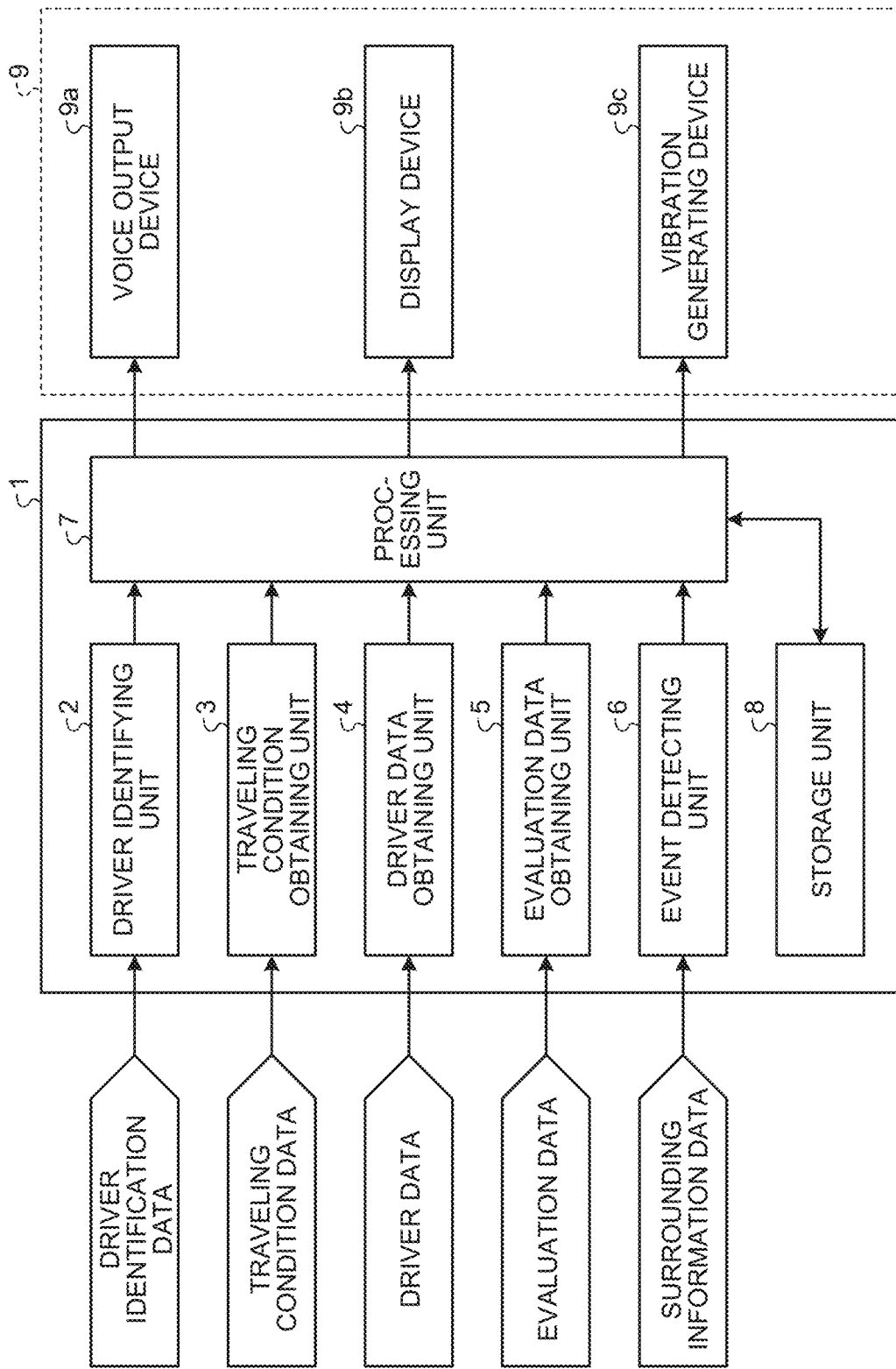
FIG. 1 is a functional block diagram illustrating an example of a driving assistance apparatus according to an embodiment.

FIG. 1 is a functional block diagram illustrating an example of a driving assistance apparatus 1 according to the embodiment. The driving assistance apparatus 1 illustrated in FIG. 1 is installed in a vehicle, such as a car, for example, and assists a driver driving the vehicle. The driving assistance apparatus 1 may be provided as an independent onboard apparatus or may be provided as a part of onboard equipment, such as drive recorder equipment or car navigation equipment, for example.

As illustrated in FIG. 1, the driving assistance apparatus 1 includes a driver identifying unit 2, a traveling condition obtaining unit 3, a driver data obtaining unit 4, an evaluation data obtaining unit 5, an event detecting unit 6, a processing unit 7, and a storage unit 8. The driving assistance apparatus 1 may include an output unit 9. For this embodiment, the driving assistance apparatus 1 described hereinafter as an example includes the output unit 9.

The driver identifying unit 2 identifies a driver driving a vehicle. The driver identifying unit 2 obtains driver identification data. The driver identification data may be obtained by any of various methods. For example, in a case where an input device not illustrated in the drawings is provided in the driving assistance apparatus 1, a driver may input the driver's own name via the input device. Furthermore, in a case where an onboard camera that is able to capture images of a driver is installed in a vehicle, the driver may be identified by image processing of video data captured by the onboard camera, for example. In this case, the video data captured by the onboard camera serves as the driver identification data. In a case where a detecting device that detects information on a driver license is installed in a vehicle, for example, the driver identifying unit 2 may be configured to obtain the driver identification data that is a result of detection by the detecting device and to identify the driver on the basis of the driver identification data.

The traveling condition obtaining unit 3 obtains traveling condition data. In a case where a front camera that captures images that are in front of the vehicle is installed, for example, the traveling condition data includes video data captured by the front camera. The traveling condition data includes data (OBD data) used in onboard diagnostics (OBD). The OBD data includes velocity data indicating velocity of the vehicle.

The driver data obtaining unit 4 obtains driver data. In a case where a vital data detecting unit that detects vital data of a driver is installed in a vehicle, for example, the driver data includes the vital data detected by the vital data detecting unit. In a case where an onboard camera that is able to capture images of the face of a driver is installed in a vehicle and lines of sight of the driver who is driving are able to be measured on the basis video data captured by this onboard camera, for example, the driver data includes data on the lines of sight.

The evaluation data obtaining unit 5 obtains evaluation data on a driver identified by the driver identifying unit 2. The evaluation data obtaining unit 5 may obtain the evaluation data via a storage medium, such as a USB memory, for example, or may obtain the evaluation data via a network, such as an external server that stores the evaluation data, for example.

The evaluation data is data on evaluation of the driver's visual cognitive ability for an event that occurs when the driver is driving the vehicle. Events include individual situations or phenomena that are caused around the vehicle driven by the driver. Examples of the events include but are not limited to: a situation where another vehicle has pulled over and stopped on the side of the road ahead of the vehicle being driven by the driver; a situation where there is a pedestrian crossing a pedestrian crossing ahead of the vehicle being driven by the driver; and a situation where an oncoming vehicle travels across in front of the driver's vehicle to make a right turn when the driver's vehicle is approaching an intersection.

The events may be grouped by type, for example. Groups that may be set for the events include, for example: presence of any standing vehicle and obstacle; any pedestrian and vehicle running out; presence of any traffic lights and road sign; any traffic light change; passing any pedestrian and bicycle; passing any oncoming vehicle (going over the lane, for example); any pedestrian and bicycle crossing; and a positional relation with any oncoming vehicle at an intersection (for example, a right turn of any oncoming vehicle, or a right turn of the driver's vehicle). The events are not necessarily grouped as described above, and may be grouped according to items learned at an authorized driving school, or grouped in any other way.

The evaluation data is obtained beforehand for each driver and for each type of event, for example. The evaluation data may be based on a two-point scale to indicate whether the driver's visual cognitive ability is high or not for a type of event, as described later. The evaluation data is not necessarily based on a two-point scale and may be based on a three-point scale or a higher point scale.

The event detecting unit 6 detects an event when the vehicle is being driven, on the basis of surrounding information data. The surrounding information data is data related to a situation of the vehicle's surroundings when the vehicle is traveling. For example, in a case where a surrounding camera that captures images of the vehicle's surroundings is installed in the vehicle, the surrounding information data includes video data captured by the surrounding camera. The surrounding camera may be, for example, a front camera that captures images in front of the vehicle, a lateral camera that captures images lateral to the vehicle, or a back camera that captures images in back of the vehicle. In a case where a sensor or laser scanner that detects a situation of the vehicle's surroundings is installed in the vehicle, for example, the surrounding information data includes results of detection by the sensor or laser scanner. In a case where car navigation equipment is installed in the vehicle, the surrounding information data may include information from the car navigation equipment, such as the position of an intersection, the position of traffic lights, or the position of a disabled vehicle or an obstacle.

For example, in a case where an event is detected on the basis of video data from a surrounding camera, the event detecting unit 6 may perform pattern matching for the position, size, and range of a target included in the video data and detect occurrence of an event corresponding to a predetermined pattern that has been calculated beforehand if a pattern similar to the predetermined pattern is detected. Calculation of the predetermined pattern may be performed beforehand on the basis of plural sets of image data representing an event identical to that event and a result of the calculation may be stored in the storage unit 8 beforehand. Events are not necessarily detected by the above described method. Events may be detected using AI trained by machine learning of events.

In a case where an event is detected by the event detecting unit 6, the processing unit 7 determines, on the basis of evaluation data on a driver related to the event detected, whether or not notification information is to be output from the output unit 9. In this case, the processing unit 7 first determines which group of the above described plural groups the detected event belongs to and obtains evaluation data for the group that the event belongs to. Next, in a case where the evaluation in the obtained evaluation data indicates that the driver's visual cognitive ability is high, the processing unit 7 determines that notification information is not to be output. In a case where the evaluation in the obtained evaluation data indicates that the driver's visual cognitive ability is not high, the processing unit 7 determines that notification information is to be output. In a case where the processing unit 7 determines that notification information is to be output, the processing unit 7 causes the output unit 9 to output notification information. In a case where the evaluation in the evaluation data is based on a three-point scale, notification information to be output by the output unit 9 may be changed according to the evaluation. For example, according to the evaluation in the evaluation data, the processing unit 7 may adjust the number, combination, and output (the degree of output, such as the volume of sound, brightness of display, or intensity of vibration, and the length of output time period) of devices to output the notification information, the devices being selected from a voice output device 9a, a display device 9b, and a vibration generating device 9c.

The processing unit 7 may make, on the basis of traveling condition data obtained by the traveling condition obtaining unit 3, a determination related to output of notification information. For example, in a case where the velocity of a vehicle is equal to or less than a predetermined threshold, the processing unit 7 may make a determination, regardless of the evaluation data, to: cause output of notification information to be not performed; decrease the degree of output; or decrease the length of output time period. In a case where the velocity of the vehicle exceeds the predetermined threshold, the processing unit 7 may make a determination, regardless of the evaluation data, to: cause output of notification information to be performed; increase the degree of output of the notification information; or increase the length of output time period.

The processing unit 7 may make, on the basis of driver data obtained by the driver data obtaining unit 4, a determination related to output of notification information. For example, in a case where vital data different from those usually obtained is obtained, such as a case where the body temperature in the driver's vital data exceeds the normal body temperature or a case where the pulse rate or respiration rate in the driver's vital data exceeds the normal value, the processing unit 7 may make a determination, regardless of the evaluation data, to: cause output of notification information to be performed; increase the degree of output of the notification information; or increase the length of output time period.

Furthermore, in a case where an event is detected by the event detecting unit 6, for example, the processing unit 7 obtains line-of-sight data on the driver and determines whether or not the driver has failed to notice the event. In a case where the processing unit 7 determines that the driver has failed to notice the event, the processing unit 7 may make a determination, regardless of the evaluation data, to: cause output of notification information to be performed; increase the degree of output of the notification information; or increase the length of output time period.

The storage unit 8 stores therein various types of data. The storage unit 8 stores therein, for example, the above described driver identification data, traveling condition data, driver data, and evaluation data, as well as data to be used for detection of an event. Furthermore, the storage unit 8 stores therein a driving assistance program that causes a computer to execute: a process of identifying a driver driving a vehicle; a process of obtaining evaluation data on the driver's visual cognitive ability for an event that occurs when the driver is driving the vehicle; a process of detecting whether or not an event has occurred on the basis of surrounding information data indicating a situation of the vehicle's surroundings; and a process of determining, in a case where the event is detected and on the basis of the evaluation data on the driver, the evaluation data being related to the event, whether or not notification information is to be output from the output unit 9, and causing the output unit 9 to output the notification information in a case where it has been determined that the notification information is to be output.

The output unit 9 outputs notification information according to a command from the processing unit 7. The notification information includes a warning to the driver. Examples of the output unit 9 include the voice output device 9a, such as a speaker, the display device 9b capable of displaying an image, and the vibration generating device 9c, such as a vibrator. An external portable terminal device, such as a mobile phone, a smartphone, or a tablet, may be used as the output unit 9, for example.

Figure 2:
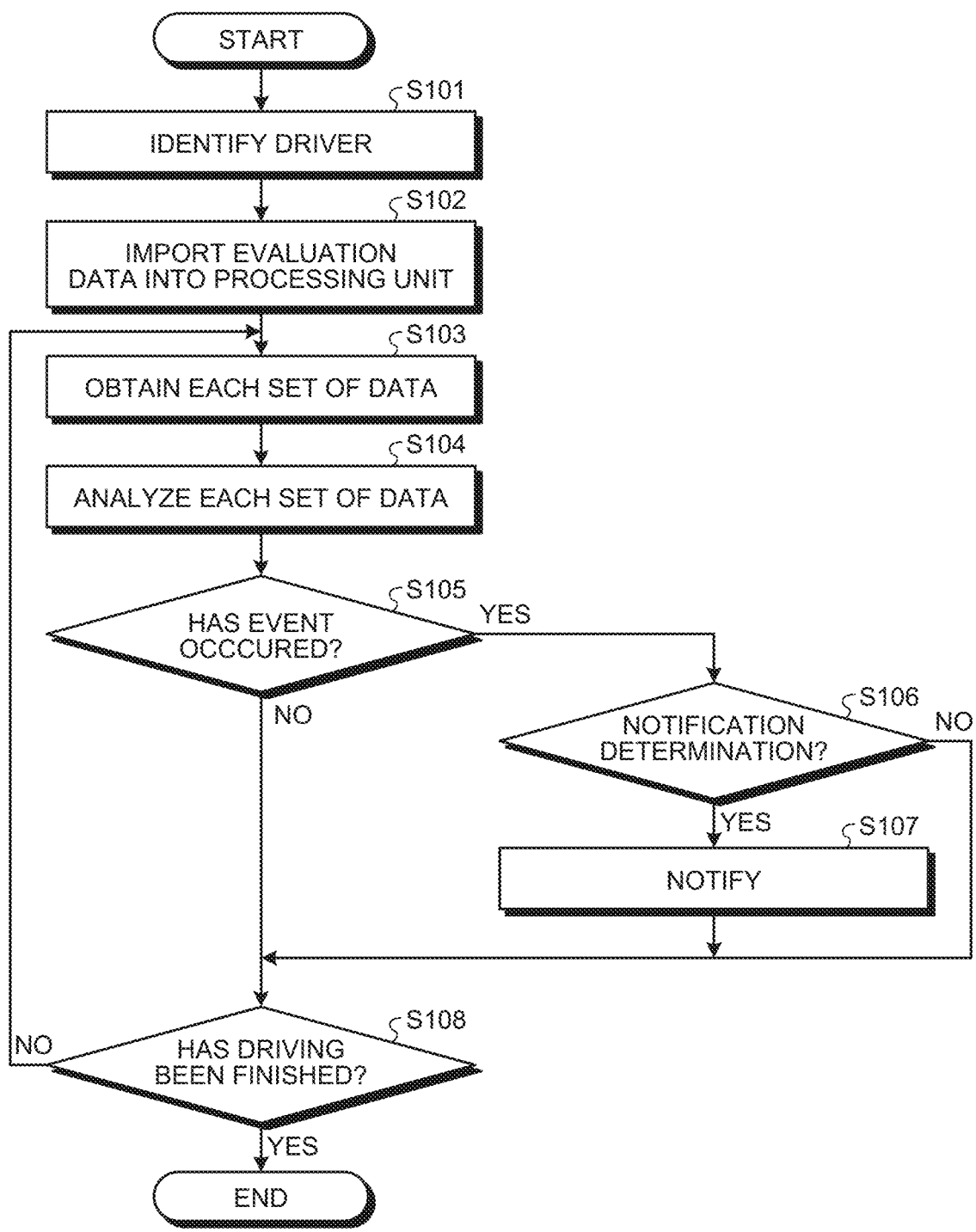
FIG. 2 is a flowchart illustrating an example of a driving assistance method according to the embodiment.

An example of a driving assistance method according to the embodiment will be described next while reference is made to FIG. 2. FIG. 2 is a flowchart illustrating the example of the driving assistance method according to the embodiment. In the driving assistance method according to the embodiment, the driver identifying unit 2 identifies a driver on the basis of driver identification data, as illustrated in FIG. 2 (Step S101). The evaluation data obtaining unit 5 obtains evaluation data on the identified driver (Step S102).

After the evaluation data is obtained, the traveling condition obtaining unit 3, the driver data obtaining unit 4, and the event detecting unit 6 respectively obtain traveling condition data, driver data, and surrounding information data (Step S103). The event detecting unit 6 analyzes, on the basis of the surrounding information data obtained, whether or not an event has occurred (Step S104).

In a case where an event has occurred (Yes at Step S105), the processing unit 7 makes a determination on whether or not notification information is to be output from the output unit 9 (Step S106). In a case where it has been determined that notification information is to be output as a result of the determination at Step S106 (Yes at Step S106), the processing unit 7 causes the output unit 9 to output notification information (Step S107).

In a case where an event has not occurred at Step S105 (No at Step S105), and in a case where it has been determined at Step S106 that notification information is not to be output (No at Step S106), the processing unit 7 determines whether or not the driver has finished driving the vehicle (Step S108). If the driver has finished driving the vehicle (Yes at Step S108), the processing is ended. If the driver has not finished driving the vehicle (No at Step S108), the processing from Step S103 is repeatedly executed.

Evaluation Data and Evaluation Apparatus

Figure 3:
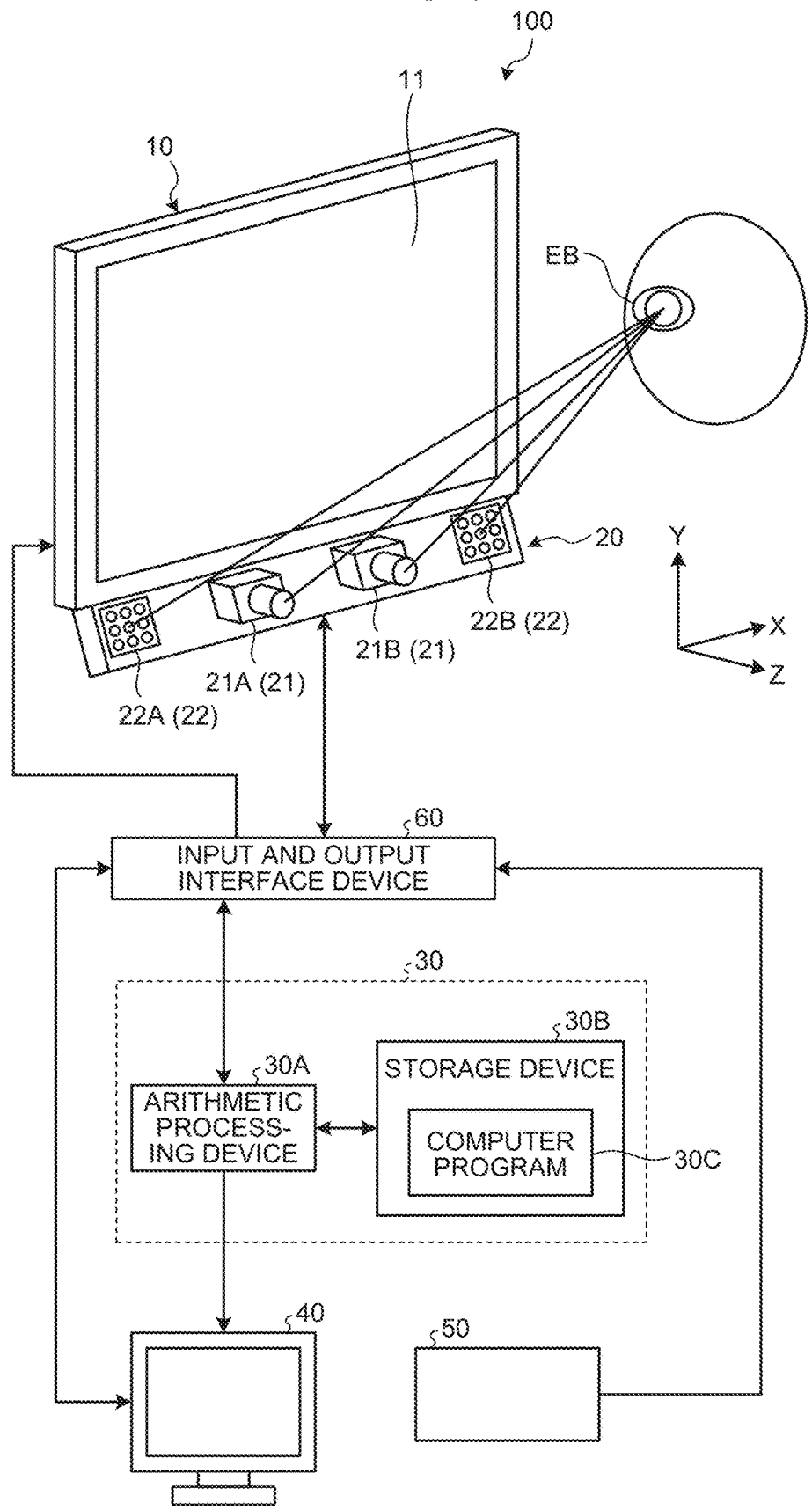
FIG. 3 is a diagram illustrating an example of an evaluation apparatus for obtaining evaluation data.

FIG. 3 is a diagram illustrating an example of an evaluation apparatus for obtaining evaluation data. An evaluation apparatus 100 according to the embodiment performs evaluation of cognitive ability for an event that occurs when a vehicle is traveling, by performing detection of lines of sight of a subject and using results of the detection. The evaluation apparatus 100 may detect a line of sight of the subject by any of various methods including, for example, a method of detecting the line of sight on the basis of positions of pupils of the subject and positions of corneal reflex images, and a method of detecting the line of sight on the basis of positions of corners of the eyes of the subject and positions of the irises.

As illustrated in FIG. 3, the evaluation apparatus 100 includes a display device 10, an image acquisition device 20, a computer system 30, an output device 40, an input device 50, and an input and output interface device 60. The display device 10, the image acquisition device 20, the computer system 30, the output device 40, and the input device 50 perform data communication via the input and output interface device 60. The display device 10 and the image acquisition device 20 each have a driving circuit not illustrated in the drawings.

The display device 10 includes a flat-panel display, such as a liquid crystal display (LCD) or an organic electroluminescence display (OLED). In this embodiment, the display device 10 has a display unit 11. The display unit 11 displays information, such as an image. The display unit 11 is substantially parallel to an X-Y plane. An X-axis direction is a left-right direction of the display unit 11, a Y-axis direction is an up-down direction of the display unit 11, and a Z-axis direction is a depth direction orthogonal to the display unit 11. The display device 10 may be a head-mounted display device. In a case where the display device 10 is a head-mounted display device, a configuration like the image acquisition device 20 is arranged in a head-mounted module. Furthermore, the display device 10 may be, for example, a display device installed in a driving simulator.

The image acquisition device 20 acquires image data on left and right eyeballs EB of a subject and transmits the image data acquired, to the computer system 30. The image acquisition device 20 has an image capturing device 21. The image capturing device 21 acquires the image data by capturing images of the left and right eyeballs EB of the subject. The image capturing device 21 has any of various cameras corresponding to methods of detecting lines of sight of subjects. For example, for a method of detecting lines of sight on the basis of the positions of pupils of a subject and positions of corneal reflex images, the image capturing device 21 has an infrared camera and has, for example: an optical system that allows transmission of near-infrared light having a wavelength of 850 nm; and an imaging element that is capable of receiving that near-infrared light. For a method of detecting lines of sight on the basis of positions of corners of a subject's eyes and positions of the irises, the image capturing device 21 has a visible camera. The image capturing device 21 outputs a frame synchronization signal. The frame synchronization signal may have a period of 20 msec, for example, but the period is not limited to this example. The image capturing device 21 may have a stereo camera configuration having a first camera 21A and a second camera 21B, for example, but is not limited to this configuration.

Furthermore, for a method of detecting lines of sight on the basis of positions of pupils of a subject and positions of corneal reflex images, the image acquisition device 20 has an illuminating device 22 that illuminates eyeballs EB of the subject. The illuminating device 22 includes a light emitting diode (LED) light source and is capable of emitting near-infrared light having a wavelength of 850 nm, for example. For a method of detecting lines of sight on the basis of positions of corners of the eyes of a subject and positions of the irises, for example, the illuminating device 22 may be not provided. The illuminating device 22 emits detection light in synchronization with a frame synchronization signal from the image capturing device 21. The illuminating device 22 may have a first light source 22A and a second light source 22B, for example, but is not limited to this example.

The computer system 30 integrally controls operation of the evaluation apparatus 100. The computer system 30 includes an arithmetic processing device 30A and a storage device 30B. The arithmetic processing device 30A includes a microprocessor, like a central processing unit (CPU). The storage device 30B includes a memory or storage like a read only memory (ROM) and a random access memory (RAM). The arithmetic processing device 30A performs arithmetic processing, according to a computer program 30C stored in the storage device 30B.

The output device 40 includes a display device like a flat-panel display. The output device 40 may include a printing device. By being manipulated, the input device 50 generates input data. The input device 50 includes a keyboard or mouse that is for a computer system. The input device 50 may include a touch sensor provided in a display unit of the output device 40, the display unit being the display device.

The display device 10 and computer system 30 in the evaluation apparatus 100 according to this embodiment are separate devices. The display device 10 and the computer system 30 may be integral with each other. For example, the evaluation apparatus 100 may include a tablet personal computer. In this case, the tablet personal computer may have, installed therein, a display device, an image acquisition device, a computer system, an input device, and an output device, for example.

Figure 4:
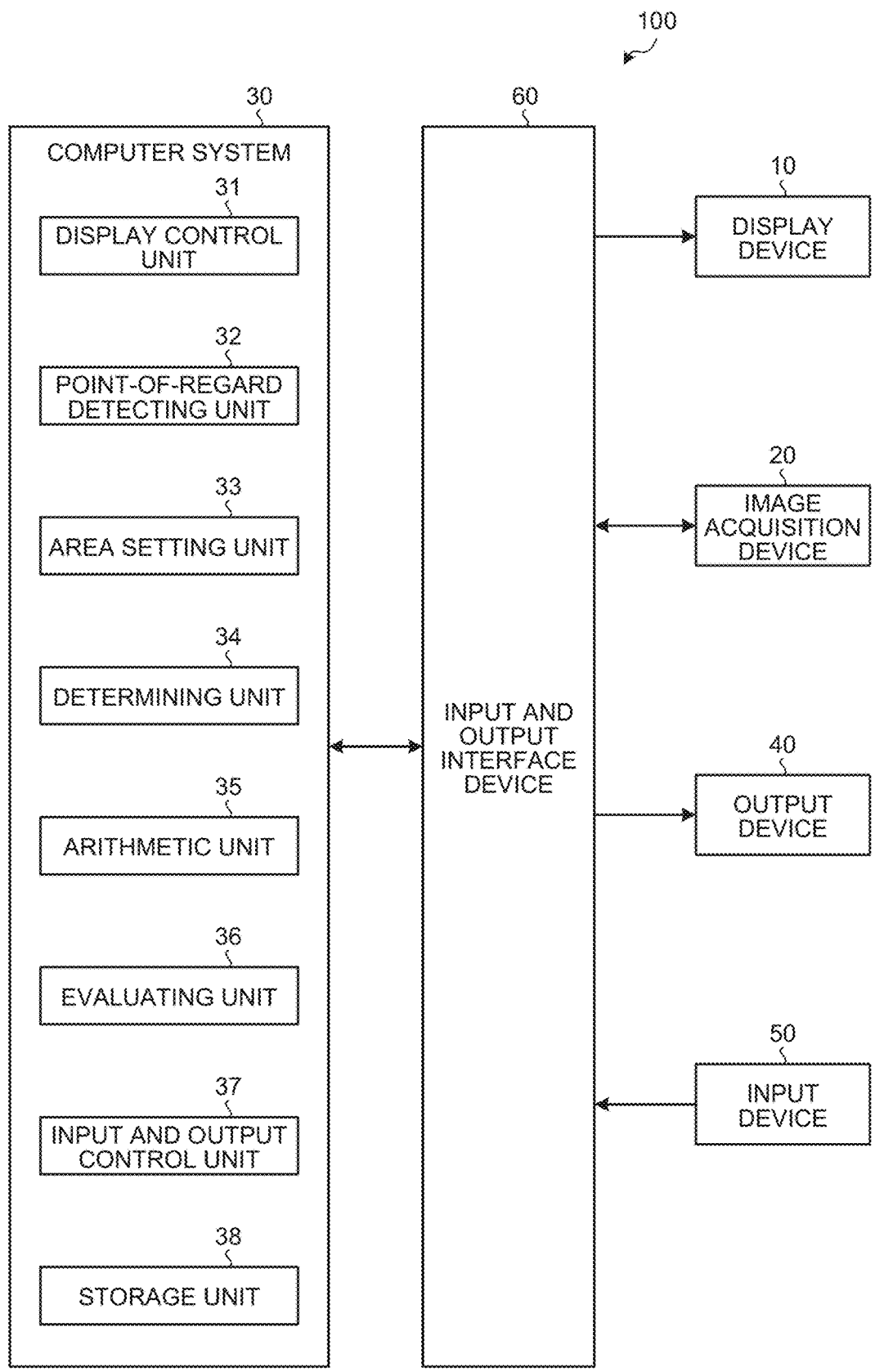
FIG. 4 is a functional block diagram illustrating the example of the evaluation apparatus.

FIG. 4 is a functional block diagram illustrating the example of the evaluation apparatus 100. As illustrated in FIG. 4, the computer system 30 has a display control unit 31, a point-of-regard detecting unit 32, an area setting unit 33, a determining unit 34, an arithmetic unit 35, an evaluating unit 36, an input and output control unit 37, and a storage unit 38. Functions of the computer system 30 are exerted by the arithmetic processing device 30A and the storage device 30B (see FIG. 3). Some of functions of the computer system 30 may be provided outside the evaluation apparatus 100.

The display control unit 31 displays an evaluation image on the display unit 11. In this embodiment, an evaluation image is an image related to an event described above.

The display control unit 31 may display the above mentioned evaluation image and instruction information as a moving image, for example, on the display unit 11. The mode of display is not limited to this example, and a still image may be displayed instead.

The point-of-regard detecting unit 32 detects positional data on a point of regard of a subject. In this embodiment, the point-of-regard detecting unit 32 detects an eye vector of the subject, the eye vector being prescribed by a three-dimensional global coordinate system, on the basis of image data on left and right eyeballs EB of the subject, the image data being obtained by the image acquisition device 20. The point-of-regard detecting unit 32 detects positional data on an intersecting point between the detected eye vector of the subject and the display unit 11 of the display device 10, this positional data serving as the positional data on the point of regard of the subject. That is, positional data on a point of regard in this embodiment is positional data on an intersecting point between an eye vector of a subject and the display unit 11 of the display device 10, the eye vector being prescribed by a three-dimensional global coordinate system. The point-of-regard detecting unit 32 detects positional data on a point of regard of a subject for every prescribed sampling period. This sampling period may be the period (for example, every 20 msec) of a frame synchronization signal output from the image capturing device 21, for example.

The area setting unit 33 sets a determination area in a part of an evaluation image on the display unit 11. In this embodiment, the determination area set by the area setting unit 33 is not displayed on the display unit 11 as a general rule. The determination area may be displayed on the display unit 11 by control of the display control unit 31, for example.

The determining unit 34 makes a determination, on the basis of positional data on each point of regard, whether or not the point of regard is in the determination area and outputs a result of the determination as determination data. The determining unit 34 determines whether or not a point of regard is in the determination area for every prescribed determination period. This determination period may be the period (for example, every 20 msec) of a frame synchronization signal output from the image capturing device 21, for example. That is, the determination period of the determining unit 34 is identical to the sampling period of the point-of-regard detecting unit 32. Every time a position of a point of regard is sampled by the point-of-regard detecting unit 32, the determining unit 34 makes a determination for that point of regard and outputs determination data. In a case where plural determination areas are set, the determining unit 34 may determine whether or not a point of regard is present, for every determination area, and output determination data.

On the basis of determination data from the determining unit 34, the arithmetic unit 35 calculates point-of-regard data for a case where a point of regard is in a determination area A1, A2, or A3 in a time period over which the determination area A1, A2, or A3 is set as described above. The arithmetic unit 35 calculates arrival time period data and duration time period data, for example, that both serve as point-of-regard data. Arrival time period data indicates a time period up to an arrival time point at which a point of regard reached the determination area first. Duration time period data indicate a duration time period over which the point of regard was in the determination area in a display time period of an event. The arithmetic unit 35 has a timer that detects an elapsed time period from display of an evaluation image on the display unit 11, and a counter that counts the number of times the determining unit 34 determines that a point of regard is in the determination area.

The evaluating unit 36 obtains evaluation data on a subject on the basis of the course of movement of a point of regard. The evaluation data includes data on evaluation of whether the subject has been able to notice and recognize an event displayed on the display unit 11.

The input and output control unit 37 obtains data (image data on eyeballs EB and/or input data, for example) from at least one of the image acquisition device 20 and the input device 50. Furthermore, the input and output control unit 37 outputs data to at least one of the display device 10 and the output device 40. The input and output control unit 37 may output a task for a subject from the output device 40, such as a speaker, for example.

The storage unit 38 stores therein determination data, point-of-regard data (arrival time period data and duration time period data), and evaluation data, which have been described above.

An evaluation method according to the embodiment will be described next. In the evaluation method according to the embodiment, cognitive ability for events that occur while a vehicle is traveling is evaluated by using the evaluation apparatus 100 described above.

Figure 5:
FIG. 5 is a diagram illustrating an example of an evaluation image to be displayed on a display unit.
Figure 6:
FIG. 6 is a diagram illustrating another example of the evaluation image to be displayed on the display unit.
Figure 7:
FIG. 7 is a diagram illustrating yet another example of the evaluation image to be displayed on the display unit.

FIG. 5 to FIG. 7 are diagrams illustrating examples of evaluation images IM1 to IM3 displayed on the display unit 11. As illustrated in FIG. 5 to FIG. 7, the display control unit 31 displays, on the display unit 11, the evaluation images IM1 to IM3 that are images for a case where a driver looks ahead from the driver's seat of a car. The evaluation images IM1 to IM3 each include an event that occurs while the vehicle is traveling.

The evaluation image IM1 illustrated in FIG. 5 includes an event E1 where another car with blinking tail lamps has stopped in front of the driver's car. This event E1 is an example of the presence of any standing vehicle and obstacle. The area setting unit 33 sets a determination area A1 in an area that is in the evaluation image IM1 and that is related to the event E1. In this case, the area setting unit 33 may set the determination area A1 in an area including the tail lamps of the other car.

The evaluation image IM2 illustrated in FIG. 6 includes an event E2 where a pedestrian with a dog crosses a pedestrian crossing, for example. This event E2 is an example of any pedestrian and bicycle crossing. The area setting unit 33 sets a determination area A2 in an area that is in the evaluation image IM2 and that is related to the event E2. In this case, the area setting unit 33 may set the determination area A2 in an area including the dog and the pedestrian.

The evaluation image IM3 illustrated in FIG. 7 includes an event E3 where a right-turning car crosses in front of the driver's car at an intersection, for example. This event E3 is an example of a positional relation with any oncoming car at an intersection. The area setting unit 33 sets a determination area A3 in an area that is in the evaluation image IM3 and that is related to the event E3. In this case, the area setting unit 33 may set the determination area A3 in an area representing a back portion of the right-turning car.

The evaluation images IM1 to IM3 may be displayed on the display unit 11 in order one by one, each for a predetermined time period, as still images, for example. The evaluation images IM1 to IM3 may each be displayed on the display unit 11 as a scene in a video in a case where the vehicle travels the road while capturing images in the front, for example. In this case, the events E1 to E3 included in the evaluation images IM1 and IM3 are consecutively displayed in association with the traveling of the vehicle.

The determination areas A1 to A3 are actually not displayed on the display unit 11. In this embodiment, the determination areas A1 to A3 are circular, for example, but without being limited to this shape, the determination areas A1 to A3 may each have an oval shape, a polygonal shape, or any other shape. Events included in evaluation images are not limited to those described above, and may be other events.

In the time period over which the evaluation image IM1, IM2, or IM3 is displayed, the point-of-regard detecting unit 32 detects a position of a point of regard P of a subject every prescribed sampling period (for example, 20 msec). In a case where a position of the point of regard P of the subject is detected, the determining unit 34 determines whether or not the point of regard P of the subject is in the determination area A1, A2, or A3 and outputs determination data. Therefore, every time a position of a point of regard is sampled by the point-of-regard detecting unit 32, that is, every determination period that is identical to the sampling period described above, the determining unit 34 outputs determination data.

On the basis of determination data, the arithmetic unit 35 calculates point-of-regard data for a case where a point of regard is in the determination area A1, A2, or A3 in a time period over which the corresponding determination area A1, A2, or A3 is set. The arithmetic unit 35 calculates, as the point-of-regard data, arrival time period data and duration time period data, for example.

The arrival time period data indicates an arrival time period that is a time period from a time point of start of display of the evaluation image IM1, IM2, or IM3 to an arrival time point at which the point of regard P reaches the corresponding determination area A1, A2, or A3 first. Therefore, the arithmetic unit 35 measures, by means of a timer T1, an elapsed time period from the start of display of each of the evaluation images IM1 to IM3, performs detection of a value measured by the timer T1 at the time point when the point of regard reaches the determination area A1, A2, or A3 first, and is thereby able to obtain, as the arrival time period data, a result of the detection from the timer T1. The arrival time period in the arrival time period data corresponds to a required time period (hereinafter, referred to as an event detecting time period) from display of an event on the display unit 11 to recognition of the event by the subject.

The duration time period data indicates a duration time period over which the point of regard P was in the determination area A1, A2, or A3. In this embodiment, the larger the number of times the determining unit 34 determines that the point of regard P is in the determination area A1, A2, or A3, the longer the duration time period over which the point of regard P is able to be estimated to be in in the determination area A1, A2, or A3. Therefore, the duration time period data may be the number of times the determining unit 34 determines that the point of regard is in the determination area A1, A2, or A3. That is, the arithmetic unit 35 may use a count value CNTA1, CNTA2, or CNTA3 at the counter as duration time period data. The count value CNTA1 is the number times the point of regard is determined to be in the determination area A1. The count value CNTA2 is the number times the point of regard is determined to be in the determination area A2. The count value CNTA3 is the number times the point of regard is determined to be in the determination area A3. The duration time period in duration time period data corresponds to a time period (hereinafter, referred to as an event regarding time period) over which a subject regards an event or looks attentively at the event.

The evaluating unit 36 obtains an evaluation value on the basis of arrival time period data and duration time period data and obtains evaluation data on the basis of the evaluation value. The evaluating unit 36 is capable of obtaining an event detecting time period on the basis of the arrival time period data. For example, in a case where the arrival time period in the arrival time period data is equal to or less than a predetermined threshold (a first time period), the evaluating unit 36 can make an evaluation that the driver's visual cognitive ability is high because the event detecting time period is short. In a case where the arrival time period in the arrival time period data exceeds the predetermined threshold (the first time period), the evaluating unit 36 can make an evaluation that the driver's visual cognitive ability is not high because the event detecting time period is long. The evaluating unit 36 may evaluate the event detecting time period on a multi-point scale by providing plural thresholds, without being limited to such evaluation on a two-point scale.

Furthermore, on the basis of duration time period data, the evaluating unit 36 may evaluate an event regarding time period up to a time point at which the subject regards and recognizes an event. For example, in a case where the duration time period in the duration time period data is equal to or less than a predetermined threshold (a second time period), the evaluating unit 36 can make an evaluation that the driver's visual cognitive ability is high because the event regarding time period is short, that is, the time period up to a time point at which the driver regards and recognizes the event is short. In a case where the duration time period in the duration time period data exceeds the predetermined threshold (the second time period), the evaluating unit 36 can make an evaluation that the driver's visual cognitive ability is not high because the event regarding time period is long, that is, the time period up to a time point at which the driver regards and recognizes the event is long. The evaluating unit 36 may evaluate the event regarding time period on a multi-point scale of one to three or more by providing plural thresholds, without being limited to such evaluation on a two-point scale.

Furthermore, the evaluating unit 36 may make a final evaluation by combining an evaluation about arrival time period data and an evaluation about duration time period data. For example, in a case where the arrival time period in the arrival time period data is equal to or less than the predetermined threshold (the first time period) and the duration time period in the duration time period data is equal to or less than the predetermined threshold (the second time period), the evaluating unit 36 can make an evaluation that the driver's visual cognitive ability is high. In any of the other cases, the evaluating unit 36 can make an evaluation that the driver's visual cognitive ability is not high. Without being limited to such evaluation on a two-point scale, the evaluating unit 36 may make an evaluation of the event regarding time period on a multi-point scale of one to three or more by making an evaluation that the driver's visual cognitive ability is in the midrange in a case where one of the arrival time period and the duration time period is equal to or less than the predetermined threshold (the first time period or second time period), for example.

Furthermore, on the basis of a total time period of the arrival time period in the arrival time period data and the duration time period in the duration time period data, the evaluating unit 36 may obtain evaluation data. The total time period corresponds to a required time period from detection of the event by the subject to regarding and recognition of the event by the subject. The subject will start looking for another event after recognizing the event. Therefore, in a case where the total time period of the arrival time period and the duration time period is equal to or less than a predetermined threshold (a third time period), the time period from the occurrence of the event and the regarding and recognition of the event by the subject is short and the search for the next event is promptly performed. Therefore, the evaluating unit 36 can then make an evaluation that the driver's visual cognitive ability is high. In a case where the total time period of the arrival time period and the duration time period exceeds the predetermined threshold (the third time period), the time period from the occurrence of the event to the regarding and recognition of the event by the subject is long and time is taken until the search for the next even is started. Therefore, the evaluating unit 36 can then make an evaluation that the driver's visual cognitive ability is not high. The evaluating unit 36 may evaluate the event regarding time period on a multi-point scale of one to three or more by providing plural thresholds, without being limited to such evaluation on a two-point scale.

Figure 8:
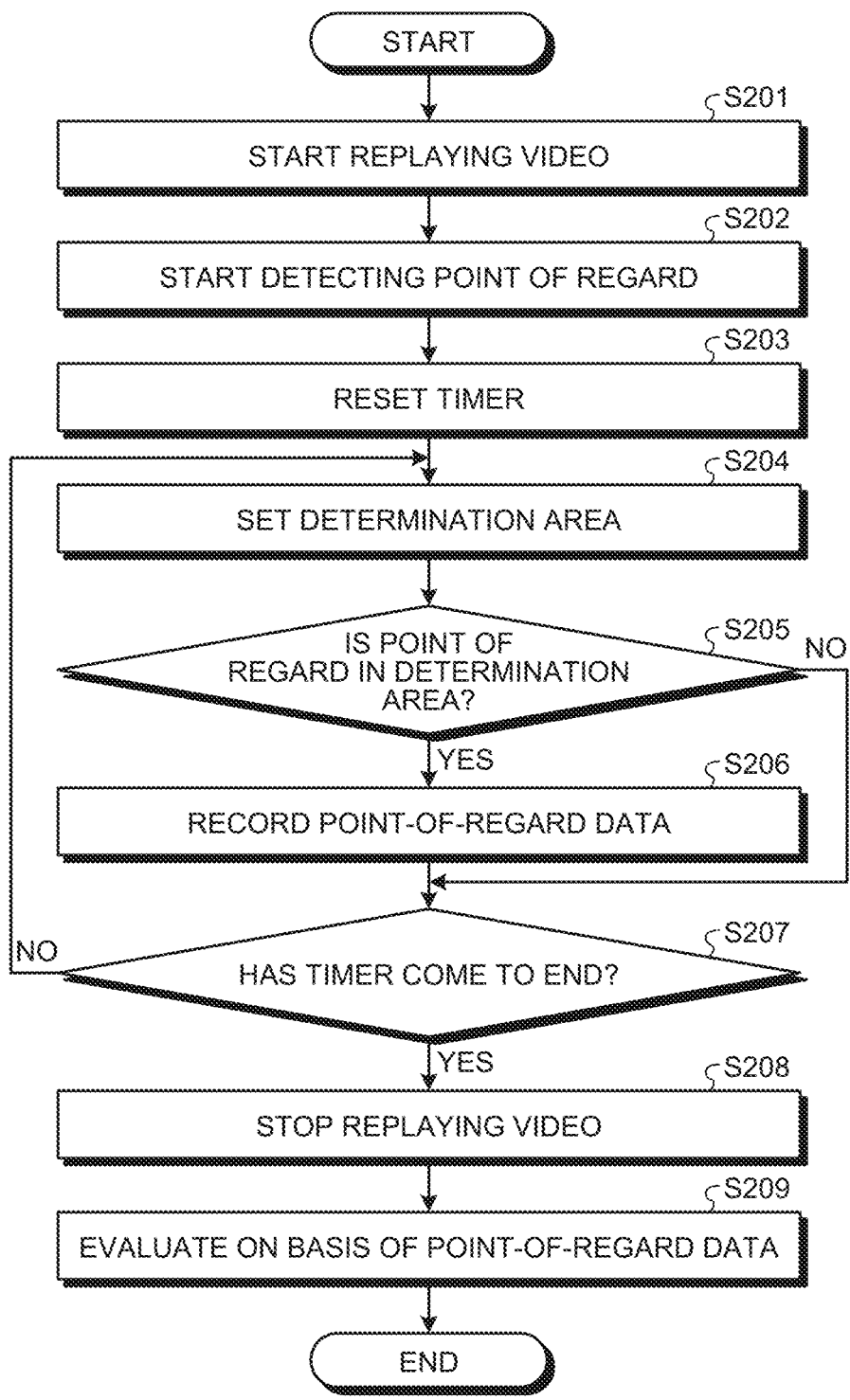
FIG. 8 is a flowchart illustrating an example of an evaluation method according to the embodiment.

An example of the evaluation method for obtaining evaluation data will be described next while reference is made to FIG. 8 to FIG. 10. FIG. 8 is a flowchart illustrating the example of the evaluation method according to the embodiment. In the evaluation method according to the embodiment, as illustrated in FIG. 8, firstly, the display control unit 31 displays the evaluation images IM1 to IM3 on the display unit 11 (Step S201). The point-of-regard detecting unit 32 starts detection of a point of regard (Step S202). The arithmetic unit 35 resets the timer (Step S203). The area setting unit 33 sets the determination areas A1 to A3 in the areas corresponding to the events E1 and E3 that are in the evaluation images IM1 to IM3 (Step S204). The determining unit 34 determines whether or not the point of regard is in the determination areas A1 to A3 (Step S205). In a case where it is determined that the point of regard is not in the determination areas A1 to A3 at Step S205 (No at Step S205), the following Step S206 is skipped and processing from Step S207 is performed. In a case where it is determined that the point of regard is in the determination areas A1 to A3 at Step S205 (Yes at Step S205), the arithmetic unit 35 stores the point of regard as arrival time period data and duration time period data, into the storage unit 38 (Step S206). At Step S206, the arithmetic unit 35 performs detection of a time at which the point of regard arrives at the determination areas A1 to A3 first and obtains a result of the detection as arrival time period data. Furthermore, in a case where it is determined that the point of regard is in the determination areas A1 to A3, the arithmetic unit 35 increments the counter values CTA1 to CNTA3 at the counter by one. The arithmetic unit 35 obtains the count values CNTA1 to CNTA3 as duration time period data.

Thereafter, in a case where the arithmetic unit 35 determines that a time at which replay of a video is to be completed has not been reached (No at Step S207), the processing from Step S204 is repeatedly performed. In a case where the arithmetic unit 35 determines that the time at which replay of the video is to be completed has been reached (Yes at Step S207), the display control unit 31 stops the replay of the evaluation images IM1 to IM3 (Step S208). After the replay of the video is stopped, the evaluating unit 36 obtains evaluation data on the basis of the arrival time period data and duration time period data that are both obtained as a result of the processing above (Step S209).

Figure 9:
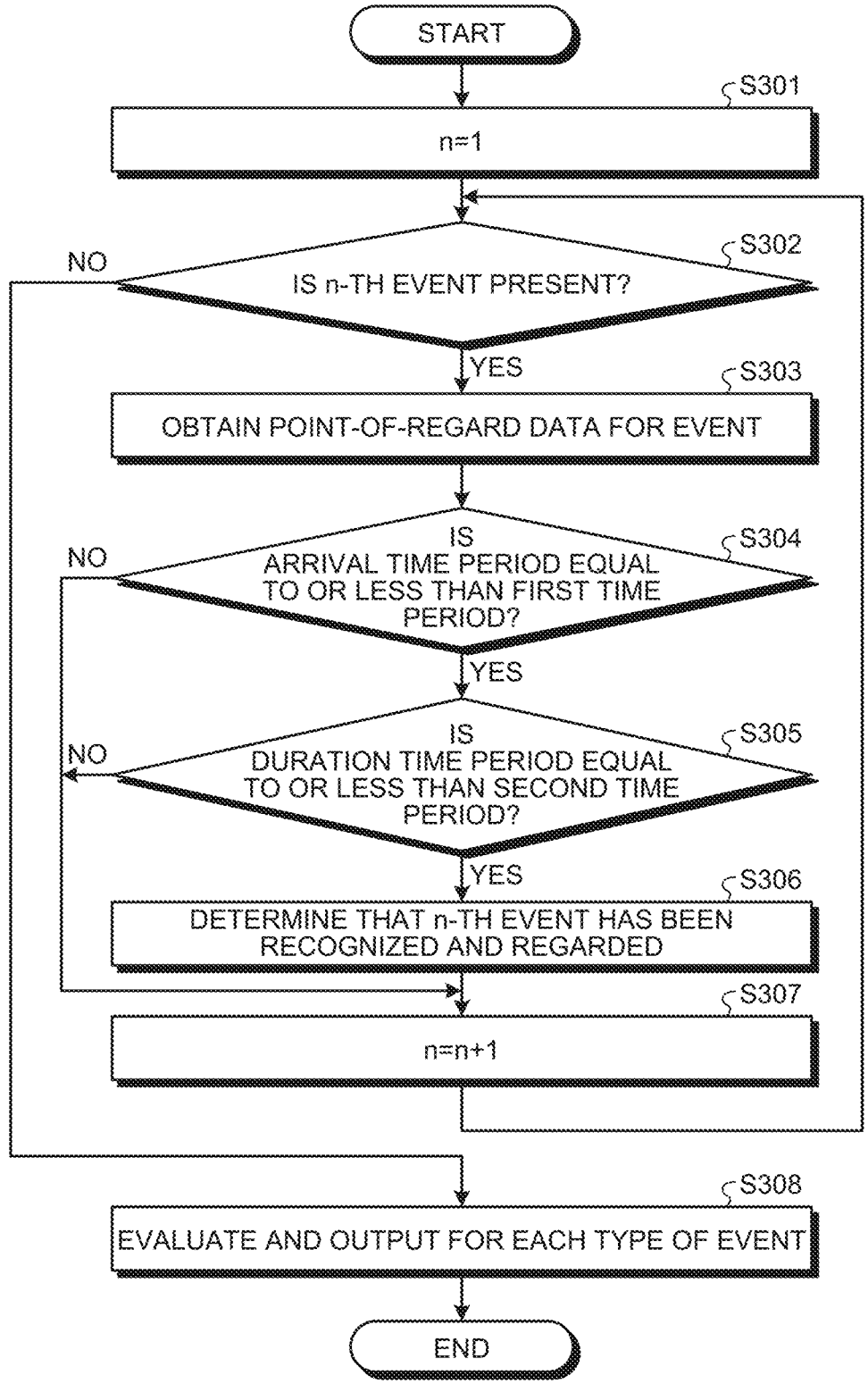
FIG. 9 is a flowchart illustrating an example of processing in a case where evaluation data is to be obtained.

FIG. 9 is a flowchart illustrating an example of processing in a case where evaluation data is to be obtained. The flow chart illustrated in FIG. 9 illustrates an example of details of the processing at Step S209 in FIG. 8. In the flowchart of FIG. 9, the number of events included in evaluation images is assumed to be n. In this embodiment, n=3 because the events E1 to E3 are included in the evaluation images IM1 to IM3. The value of n may be 3 or lower or 4 or higher.

As illustrated in FIG. 9, the evaluating unit 36 starts evaluation for n=1, that is, for the first event (Step S301). The evaluating unit 36 determines whether or not an n-th event is present (Step S302). In a case where the n-th event is present (Yes at Step S302), the evaluating unit 36 obtains point-of-regard data for the n-th event (Step S303).

On the basis of the point-of-regard data obtained, the evaluating unit 36 performs determination on whether or not a time period from start of the event to the first regarding of the event by the driver is equal to or less than the first time period (Step S304). At Step S304, the evaluating unit 36 performs determination on whether or not the arrival time period in the arrival time period data is equal to or less than the first time period.

In a case where the arrival time period is equal to or less than the first time period as a result of the determination at Step S304 (Yes at Step S304), the evaluating unit 36 performs determination on whether or not the event regarding time period over which the driver regards the event is equal to or less than the second time period (Step S305). At Step S305, the evaluating unit 36 performs determination on whether or not the duration time period in the duration time period data is equal to or less than the second time period.

In a case where the arrival time period is equal to or less than the second time period as a result of the determination at Step S305 (Yes at Step S305), the evaluating unit 36 determines that the n-th event has been promptly noticed and recognized (Step S306). Thereafter, the evaluating unit 36 starts evaluation for n=n+1, that is, for the next event (Step S307) and repeatedly performs the processing from Step S302.

On the contrary, in a case where the arrival time period exceeds the first time period as a result of the determination at Step S304 (No at Step S304), or in a case where the arrival time period exceeds the second time period as a result of the determination at Step S305 (No at Step S305), the evaluating unit 36 starts evaluation for n=n+1, that is, for the next event, without performing the determination at Step S306 (Step S307) and repeatedly performs the processing from Step S302.

The evaluating unit 36 may omit one of Step S304 and Step S305. In this case, in a case where the result of the determination at the step not omitted of Step S304 and Step S305 is "Yes", the evaluating unit 36 performs the later processing at Step S306. In a case where the result of the determination at the step not omitted is "No", the determination at Step S306 is not performed and the processing at Step S307 is performed.

In a case where the n-th event is not present at Step S302 (No at Step S302), the evaluating unit 36 performs evaluation of the driver's visual cognitive ability and performs output, for each type of the n events (Step S308). In this processing at Step S308, in a case where the determination at Step S306 has been done, the evaluating unit 36 can make an evaluation that the driver's visual cognitive ability is high for that event. In a case where the determination at Step S306 has not been done, the evaluating unit 36 can make an evaluation that the driver's visual cognitive ability is not high for that event. The evaluating unit 36 ends processing after performing the evaluation and output.

Figure 10:
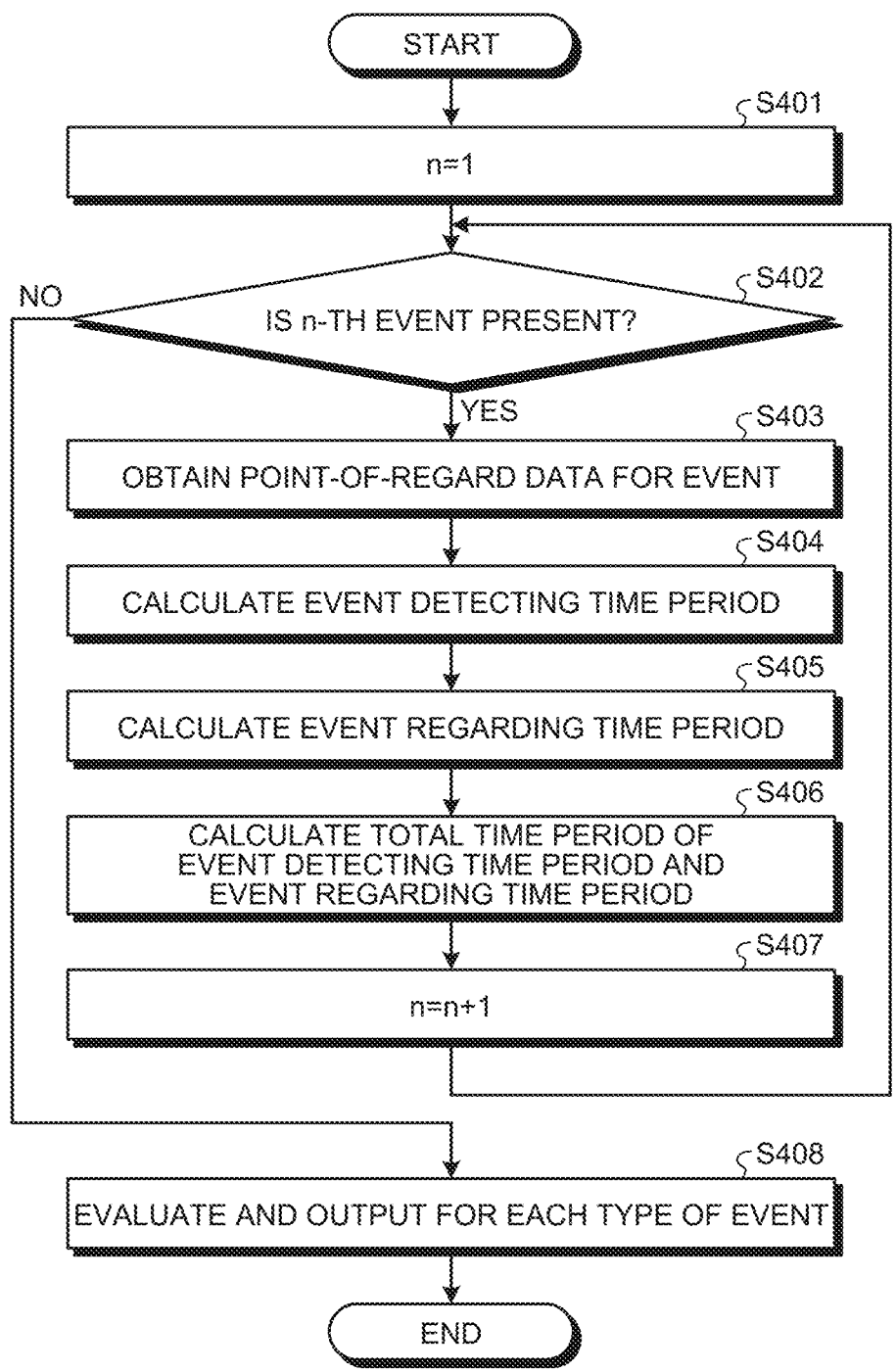
FIG. 10 is a flowchart illustrating another example of the processing in the case where evaluation data is to be obtained.

FIG. 10 is a flowchart illustrating another example of the processing in the case where evaluation data is to be obtained. The flowchart illustrated in FIG. 10 illustrates an example of details of the processing at Step S209 in FIG. 8. In the flowchart of FIG. 10, the number of events included in evaluation images is assumed to be n. In this embodiment, n=3 because the events E1 to E3 are included in the evaluation images IM1 to IM3. The value of n may be 3 or lower or 4 or higher.

As illustrated in FIG. 10, the evaluating unit 36 starts evaluation for n=1, that is, the first event, similarly to the example illustrated in FIG. 9 (Step S401). The evaluating unit 36 determines whether or not an n-th event is present (Step S402). In a case where the n-th event is present (Yes at Step S402), the evaluating unit 36 obtains point-of-regard data for the n-th event (Step S403).

On the basis of the point-of-regard data obtained, the evaluating unit 36 calculates an event detecting time period from start of the event to the first regarding of the event by the driver (Step S404). The event detecting time period corresponds to arrival time period data calculated at the arithmetic unit 35. Therefore, the evaluating unit 36 may implement the processing at S404 by obtaining the arrival time period data.

On the basis of the point-of-regard data obtained, the evaluating unit 36 calculates an event regarding time period over which the event was regarded by the driver (Step S405). The event regarding time period corresponds to duration time period data calculated at the arithmetic unit 35. Therefore, the evaluating unit 36 may implement the processing at S405 by obtaining the duration time period data.

The evaluating unit 36 calculates a total time period of the event detecting time period and the event regarding time period (Step S406). In this case, the evaluating unit 36 calculates a total time period of the arrival time period in the arrival time period data and the duration time period in the duration time period data, for example. The evaluating unit 36 stores the calculated total time period into the storage unit 38. Thereafter, the evaluating unit 36 starts evaluation for n=n+1, that is, for the next event (Step S407) and repeatedly performs the processing from Step S402.

At Step S402, in a case where the n-th event is not present (No at Step S402), the evaluating unit 36 performs evaluation of the driver's visual cognitive ability and performs output, for each type of the n events (Step S408). In the processing at Step S408, in a case where the total time period calculated at Step S406 is equal to or less than the third time period, for example, the evaluating unit 36 can make an evaluation that the driver's visual cognitive ability is high. In a case where the total time period calculated at Step S406 exceeds the third time period, for example, the evaluating unit 36 can make an evaluation that the driver's visual cognitive ability is not high for that event. The evaluating unit 36 ends processing after performing the evaluation and output.

As described above, the driving assistance apparatus 1 according to the embodiment includes: the driver identifying unit 2 that identifies a driver driving a vehicle; the evaluation data obtaining unit 5 that obtains evaluation data on the driver's visual cognitive ability for an event that occurs when the driver is driving the vehicle; the event detecting unit 6 that detects, on the basis of surrounding information data indicating a situation of the vehicle's surroundings, whether or not the event has occurred; and the processing unit 7 that determines, in a case where the event has been detected and on the basis of the evaluation data on the driver, the evaluation data being related to the event, whether or not notification information is to be output from the output unit 9, and causes the output unit 9 to output the notification information in a case where the processing unit 7 has determined that the notification information is to be output.

A driving assistance method according to the embodiment includes: identifying a driver driving a vehicle; obtaining evaluation data on the driver's visual cognitive ability for an event that occurs when the driver is driving the vehicle; detecting, on the basis of surrounding information data indicating a situation of the vehicle's surroundings, whether or not the event has occurred; and determining, in a case where the event has been detected and on the basis of the evaluation data on the driver, the evaluation data being related to the event, whether or not notification information is to be output from the output unit 9 and causing the output unit 9 to output the notification information in a case where it has been determined that the notification information is to be output.

A driving assistance program according to the embodiment causes a computer to execute: a process of identifying a driver driving a vehicle; a process of obtaining evaluation data on the driver's visual cognitive ability for an event that occurs when the driver is driving the vehicle; a process of detecting, on the basis of surrounding information data indicating a situation of the vehicle's surroundings, whether or not the event has occurred; and a process of determining, in a case where the event has been detected and on the basis of the evaluation data on the driver, the evaluation data being related to the event, whether or not notification information is to be output from the output unit 9 and causing the output unit 9 to output the notification information in a case where it has been determined that the notification information is to be output.

According to the embodiment, in a case where an event occurs when a driver is driving a vehicle, whether or not notification information is to be output to the driver is determined on the basis of evaluation data resulting from evaluation of the driver's visual cognitive ability for the event. Output of notification information every time an event occurs is thus able to be prevented and driving assistance according to the driver's visual cognitive ability is thus able to be achieved.

The driving assistance apparatus 1 according to the embodiment may further include the storage unit 8 that stores therein the evaluation data obtained, and the processing unit 7 may perform determination using the evaluation data stored in the storage unit 8. This configuration enables efficient and prompt processing at the processing unit 7.

At the driving assistance apparatus 1 according to the embodiment, the evaluation data may be obtained on the basis of: an event detecting time period from the occurrence of the event to start of regarding of the event by the driver; and an event regarding time period over which the driver regards the event. This configuration enables highly accurate evaluation of the driver's visual cognitive ability.

The driving assistance apparatus 1 according to the embodiment may further include the traveling condition obtaining unit 3 that obtains traveling condition data indicating a traveling condition of the vehicle. This configuration enables driving assistance according to the vehicle's traveling condition obtained from the traveling condition data.

The driving assistance apparatus 1 according to the embodiment may further include the driver data obtaining unit 4 that obtains driver data that is at least one of vital data and line-of-sight data on the driver, and the processing unit 7 may perform determination on the basis of the evaluation data and the driver data. This configuration enables driving assistance according to a state of the driver obtained from the vital data and line-of-sight data, for example.

The example in which evaluation of a subject's recognition capability is performed by a method of detecting lines of sight has been described above with respect to the embodiment, but without being limited to this method, the recognition capability may be evaluated by any other different method. For example, the evaluation may be performed by a method in which a touch panel is used as a display unit to display evaluation images and evaluation is performed by causing a subject to touch a target with the subject's finger. Furthermore, the evaluation may be performed by a method in which a button is pressed by the subject's foot, correspondingly to display of the target.

The technical scope of the present disclosure is not limited to the embodiment described above and modifications may be made as appropriate without departing from the gist of the present disclosure.

The present disclose enables driving assistance according to a driver's visual cognitive ability.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A driving assistance apparatus, comprising:
   a driver identifying unit that identifies a driver driving a vehicle;
   an evaluation data obtaining unit that obtains, based on an identification result of the driver identifying unit, evaluation data on the driver's visual cognitive ability for an event that occurs when the driver is driving the vehicle;
   an event detecting unit that detects whether or not the event has occurred, on the basis of surrounding information data indicating a situation of the vehicle's surroundings; and
   a processing unit that
      determines, in a case where the event has been detected and on the basis of the evaluation data on the driver, the evaluation data being related to the event, whether or not notification information is to be output from an output unit,
      does not cause the output unit to output the notification information in a case where the driver's visual cognitive ability is evaluated high, and
      causes the output unit to output the notification information in a case where the driver's visual cognitive ability is not evaluated high,
   wherein the evaluation data on the driver's visual cognitive ability is evaluation data obtained based on at least one of arrival time and duration time when an evaluation image including an event occurred while the vehicle is traveling is displayed to the driver, the arrival time being a period from a time point of start of display of the evaluation image to a time point at which a point of regard of the driver reaches a determination area first, the determination area being an area related to an event included in the evaluation image, the duration time being a period over which the point of regard of the driver is in the determination area, the evaluation data evaluating whether the driver's visual cognitive ability is high or not by any of methods (a) to (c):
   (a) when the arrival time is less than a first predetermined time or when the duration time is less than a second predetermined time, evaluating that the driver's visual cognitive ability is high, or otherwise, evaluating that the driver's visual cognitive ability is not high,
   (b) when the arrival time is less than the first predetermined time and the duration time is less than the second predetermined time, evaluating that the driver's visual cognitive ability is high, or otherwise, evaluating that the driver's visual cognitive ability is not high, and
   (c) when a total time of the arrival time and the duration time is less than a third predetermined time, evaluating that the driver's visual cognitive ability is high, or otherwise, evaluating that the driver's visual cognitive ability is not high.

2. The driving assistance apparatus according to claim 1, further comprising:
   a storage unit that stores therein the evaluation data obtained, wherein
   the processing unit performs determination by using the evaluation data stored in the storage unit.

3. The driving assistance apparatus according to claim 1, further comprising:
   a traveling condition obtaining unit that obtains traveling condition data indicating a traveling condition of the vehicle, wherein
   the processing unit performs determination on the basis of the evaluation data and the traveling condition data.

4. The driving assistance apparatus according to claim 1, further comprising:
   a driver data obtaining unit that obtains driver data that is at least one of vital data and line-of-sight data on the driver, wherein
   the processing unit performs determination on the basis of the evaluation data and the driver data.

5. The driving assistance apparatus according to claim 1, wherein the evaluation data is a data evaluated by type of the event, and
   the processing unit determines whether or not the notification information is to be output from the output unit based on the evaluation data of the driver regarding the type of the event detected by the event detecting unit.

6. A driving assistance method, including:
   identifying a driver driving a vehicle;
   obtaining, based on an identification result of the identifying, evaluation data on the driver's visual cognitive ability for an event that occurs when the driver is driving the vehicle;
   detecting whether or not the event has occurred, on the basis of surrounding information data indicating a situation of the vehicle's surroundings; and
   determining, in a case where the event has been detected and on the basis of the evaluation data on the driver, the evaluation data being related to the event, whether or not notification information is to be output from an output unit
   not causing the output unit to output the notification information in a case where the driver's visual cognitive ability is evaluated high, and
   causing the output unit to output the notification information in a case where the driver's visual cognitive ability is not evaluated high,
   the evaluation data on the driver's visual cognitive ability is evaluation data obtained based on at least one of arrival time and duration time when an evaluation image including an event occurred while the vehicle is traveling is displayed to the driver, the arrival time being a period from a time point of start of display of the evaluation image to a time point at which a point of regard of the driver reaches a determination area first, the determination area being an area related to an event included in the evaluation image, the duration time being a period over which the point of regard of the driver is in the determination area, the evaluation data evaluating whether the driver's visual cognitive ability is high or not by any of methods (a) to (c):
   (a) when the arrival time is less than a first predetermined time or when the duration time is less than a second predetermined time, evaluating that the driver's visual cognitive ability is high, or otherwise, evaluating that the driver's visual cognitive ability is not high,
   (b) when the arrival time is less than the first predetermined time and the duration time is less than the second predetermined time, evaluating that the driver's visual cognitive ability is high, or otherwise, evaluating that the driver's visual cognitive ability is not high, and
   (c) when a total time of the arrival time and the duration time is less than a third predetermined time, evaluating that the driver's visual cognitive ability is high, or otherwise, evaluating that the driver's visual cognitive ability is not high.

7. A non-transitory computer readable recording medium storing therein a driving assistance program that causes a computer to execute:
- a process of identifying a driver driving a vehicle;
- a process of obtaining, based on an identification result of the identifying, evaluation data on the driver's visual cognitive ability for an event that occurs when the driver is driving the vehicle;
- a process of detecting whether or not the event has occurred, on the basis of surrounding information data indicating a situation of the vehicle's surroundings; and
- a process of determining, in a case where the event has been detected and on the basis of the evaluation data on the driver, the evaluation data being related to the event, whether or not notification information is to be output from an output unit
- not causing the output unit to output the notification information in a case where the driver's visual cognitive ability is evaluated high, and
- causing the output unit to output the notification information in a case where the driver's visual cognitive ability is not evaluated high,
- the evaluation data on the driver's visual cognitive ability is evaluation data obtained based on at least one of arrival time and duration time when an evaluation image including an event occurred while the vehicle is traveling is displayed to the driver, the arrival time being a period from a time point of start of display of the evaluation image to a time point at which a point of regard of the driver reaches a determination area first, the determination area being an area related to an event included in the evaluation image, the duration time being a period over which the point of regard of the driver is in the determination area, the evaluation data evaluating whether the driver's visual cognitive ability is high or not by any of methods (a) to (c):
  - (a) when the arrival time is less than a first predetermined time or when the duration time is less than a second predetermined time, evaluating that the driver's visual cognitive ability is high, or otherwise, evaluating that the driver's visual cognitive ability is not high,
  - (b) when the arrival time is less than the first predetermined time and the duration time is less than the second predetermined time, evaluating that the driver's visual cognitive ability is high, or otherwise, evaluating that the driver's visual cognitive ability is not high, and
  - (c) when a total time of the arrival time and the duration time is less than a third predetermined time, evaluating that the driver's visual cognitive ability is high, or otherwise, evaluating that the driver's visual cognitive ability is not high.

* * * * *